United States Patent [19]

McCarthy et al.

[11] Patent Number: 5,618,689
[45] Date of Patent: Apr. 8, 1997

[54] ENHANCED PROCEDURES FOR PREPARING FOOD HYDROLYSATES

[75] Inventors: James G. McCarthy, Washington Depot; Dharam V. Vadehra, New Milford, both of Conn.

[73] Assignee: Nestec S.A., Vevey, Switzerland

[21] Appl. No.: 450,421

[22] Filed: May 25, 1995

[51] Int. Cl.$^6$ .................................................. C12P 21/00
[52] U.S. Cl. .......................... 435/68.1; 435/272; 426/46
[58] Field of Search .................. 435/68.1, 272; 426/46

[56] References Cited

U.S. PATENT DOCUMENTS

| | | |
|---|---|---|
| 2,180,637 | 11/1939 | Kemmerer . |
| 3,846,560 | 11/1974 | Hempenius et al. ............... 426/18 |
| 3,857,967 | 12/1974 | Kikuchi et al. . |
| 3,876,806 | 4/1975 | Hempenius et al. ............... 426/46 |
| 3,914,436 | 12/1975 | Nakadai et al. . |
| 4,009,286 | 2/1977 | Moll et al. . |
| 4,016,147 | 4/1977 | Fujimaki et al. ............... 435/68.1 |
| 4,427,658 | 1/1984 | Maubois et al. . |
| 4,587,127 | 5/1986 | Akao et al. ............... 426/46 |
| 5,039,532 | 8/1991 | Jost et al. . |
| 5,073,496 | 12/1991 | Oosterhuis et al. . |
| 5,091,308 | 2/1992 | Klegerman et al. . |
| 5,141,757 | 8/1992 | Dac et al. ............... 426/46 |
| 5,480,663 | 1/1996 | Heyland et al. ............... 426/262 |

FOREIGN PATENT DOCUMENTS

| | | |
|---|---|---|
| 1246476 | 12/1988 | Canada . |
| 0087247 | 8/1983 | European Pat. Off. . |
| 0223560 | 5/1987 | European Pat. Off. . |
| 0320717A2 | 6/1989 | European Pat. Off. . |
| 0566877A3 | 11/1993 | European Pat. Off. . |
| 153892 | 2/1982 | Germany . |
| 237078A3 | 7/1986 | Germany . |
| 53-47590 | 4/1978 | Japan . |
| 53-047590A | 4/1978 | Japan . |
| 54-143588A | 11/1979 | Japan . |
| 61-108392A | 5/1986 | Japan . |
| 04121188A | 4/1992 | Japan . |
| WO9211771 | 7/1992 | WIPO . |
| WO9324020 | 12/1993 | WIPO . |

OTHER PUBLICATIONS

Bala et al., "Stability of Sterile Beef and Beef Extract to Protease and Lipase from *Pseudomonas fragi*", Journal of Food Science vol. 44, 1294–1298 (1979).

Tanabe, et al., "Production of a High–Glutamine Oligopeptide Fraction from Gluten by Enzymatic Treatment and Evaluation of its Nutritional Effect on the Small Intestine of Rats", Journal of Food Biochemistry 16, (1993) 235–248.

Loveland, et al., "Characterization of Psychrotrophic Microorganisms Producing β–Galactosidase Activities", Applied and Environmental Microbiology, Jan. 1994, 12–18.

Trimbur, et al., "Characterization of a Psychrotrophic Arthobacter Gene and Its Cold–Active β–Galactosidase." Applied and Environmental Microbiology, Dec. 1994 4544–4552.

APS ABS. Japan 56–96679 Aug. 4, 1981 Yokoyama et al.

*Primary Examiner*—Herbert J. Lilling
*Attorney, Agent, or Firm*—Vogt & O'Donnell, LLPA

[57] ABSTRACT

A comestible hydrolysate product is prepared by hydrolyzing a proteinaceous substrate devoid of viable mesophilic microorganisms and spores in a sterile system with a sterile enzyme preparation suitable for hydrolyzing the substrate.

20 Claims, No Drawings

ENHANCED PROCEDURES FOR PREPARING FOOD HYDROLYSATES

BACKGROUND OF THE INVENTION

The present invention relates to enzymatic hydrolysis of substances, particularly proteinaceous substances and more particularly, proteinaceous food substances.

Interest in the use of enzymes to hydrolyze substances has increased significantly in industry over the past twenty-five years, particularly in the food industry, since with acid hydrolysis, which has long been employed, some essential amino acids are entirely decomposed and others are partially decomposed. In addition, it now is recognized that during hydrolysis of proteins with hydrochloric acid, by-products, including such as what are known as chlorohydrins, i.e., chloropropanol and diol compounds, which may pose health concerns, are formed.

Enzymatic hydrolysis of substances operates on the basic theme of cleavage of chemical bonds of the substance. In general, preparation of hydrolysates intended to be employed themselves as a consumable comestible product, such as for nutritional purposes, or for other uses such as flavorants or for preparation of other products, or to be employed for obtaining a particular product fraction or fractions thereof for such or other uses, for example, is effected by incorporating an enzyme preparation with an aqueous suspension of a substance under conditions wherein, for process efficacy, the substance is at least partially solubilized. The selection of the enzyme preparation and other reagents is based upon the compositional chemical structure of the substance(s) to be hydrolyzed and by a desired hydrolysate product specification.

Use of sterile lactase enzyme preparations in pasteurized or sterilized milk and milk products to break down lactose, such as referred in Bijl, Canadian Patent No. 1 246 476 is known, and it is believed that sterile enzyme preparations have been employed in the pharmaceutical industry. However, generally in the context of hydrolyzing proteins, particularly in the industrial setting for preparation of nutritional and flavorant comestible products, microbiological contamination is generally not considered problematical, since the hydrolysis procedures are carried out generally at a temperature in a range of from 50° C. to 60° C. for from about 8 hrs to about 12 hrs so that, as noted by Eriksen, et al., PCT Patent Application Publication No WO 92/11771, bacterial growth is limited. Moreover, although it is reported in the art that enzymatic hydrolysis of proteins may be carried out at temperatures less than 50° C., in general, even in such cases, microbiological contamination generally may not be of concern since the protein hydrolysate products are heated after preparation to a temperature and for a time at least sufficient to inactivate the enzymes, and use of temperatures and times to effect pasteurization or sterilization of the product are common.

On the other hand, however, it is noted that the age-old preparation of soy sauce from a koji avoids microbiological contamination with a high concentration of sodium chloride, but that, however, is not necessarily now deemed desirable for health reasons and is not, moreover, conducive for activities of many enzymes. Other agents to inhibit microorganism growth also have been employed, such as suggested by Kemmerer, U.S. Pat. No. 2,180,637, and such as employed by Kikuchi, et al., U.S. Pat. No. 3,857,967, but the agents disclosed are undesirable for food applications.

As compared with known microorganism fermentations or acid hydrolysis procedures, which have a limited capacity for tailoring the resultant products, since, generally, only the extent, or degree, of hydrolysis can be controlled readily, enzymatic hydrolysis theoretically enables, with regard to any particular substrate treated, obtaining a variety of products tailored to particular specifications with greater precision. However, even to the extent that such may be the case, as is documented throughout the art, in general particularly in terms of a cost/benefit analysis, although dependent upon the quantity of enzyme employed, yields of desired products obtained by enzymatically hydrolyzing proteins are considered low, and it is generally the rule, rather than the exception, that such procedures result in substantial amounts of by-product(s) for which uses are relatively few and not of great economic value.

A factor which impacts upon yield of desired product(s) is that enzyme preparations produced for general industrial use, known in the art as commercial-grade enzymes, generally are a mixture, or "cocktail", of a plurality of enzymes which differ in substrate affinity and specificity, hereinafter "activity", i.e., the capability of effecting a particular substrate chemical bond cleavage under any particular set of reaction conditions, including pH and temperature. Although the activity of one enzyme of the preparation cocktail generally is predominant, and although situations are known wherein two desirable activities of the enzyme preparation may be sequenced such as by pH control, as disclosed in Gianna, et al., European Patent Application Publication No. 0 320 717, the other enzyme(s) of the preparation, which may be considered "impurities", may produce results and effects which may be competitive with, or even at odds with, the desired effects and results. For example, depending upon the substrate and/or the conditions of hydrolysis, the "impurities" may detract from a theoretical yield because such may induce competitive reactions and/or even may be destructive of the enzyme having the predominant activity, thus inducing reaction inhibition beyond that which would be expected, based upon theoretical considerations.

To enhance process control and final product specificity, use of substantially pure enzymes would be desirable. However, the attendant increased enzyme preparation cost due to purification procedures generally presents a cost/benefit ratio which generally can not be justified in general industrial use, other than such as in the pharmaceutical industry, or for relatively small-scale high-value analytical purposes or bio-engineering. Such is particularly the case in the food flavorant art, particularly when the cost/benefit of purified enzyme use is compared to that of carrying out conventional microorganism fermentations or an acid hydrolysis.

To address the afore-noted problems, it is not uncommon in industrial practice, particularly in the comestible, i.e., food, art, to employ greater amounts of commercial-grade preparations to amplify the activity of the dominant enzyme of a given preparation, as compared with what theoretically would be required for any given set of processing conditions, and to carry out the reaction for about 8 hrs to about 12 hrs. For example, employing a greater amount of enzyme preparation speeds up the reaction rate for any given set of conditions, and in general, when subjecting proteinaceous substances to a moderate degree of hydrolysis to obtain a hydrolysate which has a broad peptide profile and which is comprised of constituents having a molecular weight in excess of 10,000 Daltons, difficulties are not encountered operating in this manner.

Various problems arise, however, when it is desired to obtain a protein hydrolysate, such as one suitable for nutritive applications, which has a high degree of hydrolysis so that the product contains a significant amount of free amino acids and/or a narrow peptide size-range profile, e.g., a molecular weight below about 10,000 Daltons and preferably, below about 6,000 Daltons. As is discussed in the art, such products are useful in a wide variety of food and nutritive applications, including formulas for infants allergic to milk proteins. However, unless particular reactant combinations and conditions are employed, such as in Jost, U.S. Pat. No. 5,039,532, yields of such products, as indicated above, generally are considered undesirably low, and in general, such procedures are considered to be expensive because of the enzyme preparation(s) employed. On the other hand, to reduce enzyme usage, the substrate employed may be dilute, which likewise makes process economics unattractive because of unit/volume considerations.

To obtain high-value end-use products as noted above, it also is known to combine enzymatic procedures with hydrolysate isolation procedures such as ultrafiltration. Such procedures include those disclosed in Eriksen, et al., PCT Patent Application Publication No. WO 92/11771, and in Nielsen, et al., PCT Patent Application Publication No. WO 93/24020, for example, and an alternative to separate isolation procedures has been proposed in Maubois, et al., U.S. Pat. No. 4,427,658, which discloses to employ an ultrafiltration membrane reactor, which may be used in a continuous mode, to recycle and further process a permeate. Maubois, however, indicates that the ratio of enzyme concentration to protein concentration must be on the order of 8% to 15%.

Thus, it long has been and still is desired in the food industry, particularly in the context of hydrolyzing proteins, to obtain, consistently, enzymatic hydrolysates of low molecular weight and/or of narrow peptide profile and to solve the dichotomy of how to increase yields while at the same time reducing the amount of enzyme usage to achieve cost savings and cost/benefit effectiveness.

SUMMARY OF THE INVENTION

The present invention provides a process for enzymatically hydrolyzing substances susceptible to enzymatic hydrolysis, particularly proteinaceous substances, which enables employing enzyme preparations at a temperature which enables optimizing or otherwise controlling enzymatic activity to effect a high degree of hydrolysis and enhanced control of product profile, and without employing antimicrobial agents. Significantly, particularly in the case of protein hydrolysis, the present invention enables not only obtaining the foregoing advantages, but also enables obtaining yields of low molecular weight enzymatic hydrolysis products which are at least comparable with yields of prior procedures even though employing a quantity of enzyme preparation less than heretofore generally employed in prior art enzymatic hydrolysis processes. The present invention thereby provides cost-reduction compared to prior art enzymatic processes, since enzyme utilization is a, if not the, primary processing cost concern when practicing enzymatic hydrolysis.

In addition, one may, in accordance with the process of the present invention manipulate temperature conditions of processing to enhance activity of an enzyme preparation and/or to mute or enhance activity of enzyme "impurities" of a preparation. Moreover, the process of the present invention will enable use of enzymes for manufacturing hydrolysates for food use which heretofore generally have not been considered favorably for industrial use because of their activity temperature profile.

The foregoing results are effected by a process characterized in that a substrate susceptible to enzymatic hydrolysis and devoid of viable mesophilic microorganisms and spores, particularly a proteinaceous substrate, is hydrolyzed in a sterile system with a sterile enzyme preparation suitable for hydrolyzing the substrate, i.e., cleaving the substrate.

The hydrolysis may be carried out at any temperature, including the mesophilic range, i.e., about 20° C. to about 40° C., and at temperatures below the mesophilic range, with a caveat being that the temperature is such that the enzyme(s) is/are active. To achieve additional benefits of long-term hydrolysis made available by the present invention, the hydrolysis advantageously is carried out at a temperature below the mesophilic range, preferably in the psychrophilic range, i.e., from about 0° C. to about 20° C., and more advantageously, at a temperature below 17° C. The substrate medium, however, should not be non-fluid, e.g., frozen, and thus, the hydrolysis may be carried out advantageously at a temperature of from about 0° C. to about 45° C., although higher temperatures are not precluded.

In the context of this disclosure and claims, the term "proteinaceous substrate" is intended to mean and include intact proteins, i.e., proteins per se, and peptides.

In the context of this disclosure and claims, the term "enzyme preparation" is intended to mean and include at least one enzyme in a stable form, such as in a form of a dehydrated powder, or in solution or suspension in a liquid, generally an aqueous medium, and the term is intended to include purified enzymes, as well as commercial-grade enzymes, as are known in the art.

In the context of this disclosure and claims, a "sterile" enzyme preparation is intended to mean and include that the enzyme preparation is devoid of viable microorganisms and spores thereof, i.e., fungi, yeast and bacteria, as may be achieved by known and conventional methods of sterile filtration. A sterile enzyme preparation is considered to be one which does not contain microorganisms or spores capable of passing through a membrane, i.e., filter, having 0.45 μ pores.

In addition, in cases when microorganisms and/or spores are present in the enzyme preparation, but non-viable, the term "sterile" is intended to mean that the preparation has been subjected to a procedure, including but not limited to those described below, to render microorganisms and spores associated therewith incapable of living, developing, reproducing, and/or regenerating and so that any microorganism growth resultant from the preparation, which is sought to be avoided, is no more than would be the case with a sterile-filtered preparation as described above.

In the context of this disclosure and claims, a "sterilized system" is intended to mean and include equipment suitable for carrying out enzymatic hydrolysis, including but not limited to apparatus and apparatus systems described below, which has been treated with procedures, such as with heat, U.V. or ionizing radiation or irradiation and/or alcohol wash or other like sterilizing procedures known in the art suitable for obtaining an aseptic equipment condition. Of course, the sterile condition of the system elements should be maintained prior to employing the same for processing in accordance with the present invention, to the extent possible, with known and accepted aseptic practices and procedures to avoid contamination.

Although any of known enzymatically hydrolyzable substances may be treated in accordance with the present invention, proteinaceous substances are treated advantageously for preparation of comestible products. As is illustrated further below, the present invention of applied particularly advantageously to treatment vegetable proteinaceous substances and has particular applicability for treatment of wheat gluten, herein intended to include vital gluten, and of soy protein and of corn protein and of peptides derived therefrom. In a particularly preferred embodiment in accordance with the present invention, common to treatment of such proteinaceous substrates is a final hydrolysis step, or stage, carried out as set forth above, which employs a sterile enzyme preparation suitable for cleaving a peptide, the enzyme preparation selected being dependent upon the final product specification desired. For example, for obtaining a product having high amounts of free amino acids, an exopeptidase, i.e., an aminopeptidase or a carboxypeptidase, may be employed in particular, and for obtaining high yields of such as glutamic acid or glutamyl peptides, a glutamase is employed.

Thus, preferred embodiments of the present invention for hydrolyzing proteinaceous substances are carried out most advantageously in a plurality of stages, and the invention described above is employed most advantageously as a final stage. In general, in such cases, a hydrolysate obtained by proteolytically hydrolyzing a suspension of a proteinaceous substance is treated so that mesophilic microorganisms and spores contained in the hydrolysate are rendered non-viable, and in general, rendering the microorganisms and spores non-viable is accomplished efficiently by heating the hydrolysate at a temperature and for a time sufficient to render the hydrolysate devoid of viable microoganisms and spores. The heated hydrolysate then is cooled in a manner so that it retains its sterility and then, the cooled substrate is hydrolyzed in a sterile system with a sterile enzyme preparation, as described above.

DETAILED DESCRIPTION OF THE INVENTION

As indicated above, when proteinaceous materials are treated, the advantages of the present invention may be effected by carrying out one or more enzymatic hydrolysis stages, or steps. In accordance with the present invention, when a plurality of stages are carried out, one or more steps may be carried out in accordance with the sterile hydrolysis procedure described above. However, as indicated, it generally will be found that hydrolysis in accordance with the sterile hydrolysis procedure of the invention is carried out most advantageously as a final, or last, step of a plurality of hydrolysis steps.

For example, when starting with intact proteins, for enzymatic hydrolysis to proceed efficiently, as will be appreciated by one skilled in the art, the proteinaceous substance advantageously is solubilized partially first, which aids formation of a suspension of the substance, in an aqueous medium. As also will be appreciated, depending upon the composition of the substance providing the reaction substrate, partial solubilization of the proteinaceous substance may be effected by selection of pH conditions alone. For example, corn and corn proteins and compositionally-similar substances, will be found to solubilize sufficiently at a pH of from about 8 to about 9 for facilitating hydrolysis. On the other hand, at least partial solubilization may be effected by a proteolysis procedure at a particular pH, and wheat gluten, and compositionally-similar substances, will be found to solubilize best with such a procedure.

Thus, the present invention includes processes wherein prior to the sterile hydrolysis procedure, a proteinaceous substance is hydrolyzed with a proteolytic enzyme preparation to obtain a substrate for treatment in the sterile procedure. Further, prior to carrying out the sterile procedure, a proteinaceous substance may be treated with a proteolytic enzyme preparation to solubilize protein of the substance to obtain an at least partially solubilized substrate and then, the solubilized substrate is treated with a proteolytic enzyme preparation to obtain the proteinaceous substrate for treatment in the sterile procedure, and these treatments may be carried out so that the substrate is rendered devoid of viable microorganisms and spores, such treatment being defined herein as including a heat-treatment to effect such, as discussed further below.

In addition, it may be desired to pretreat a substrate in accordance with procedures such as set forth in the PCT Applications noted above or in accordance with procedures such as disclosed in Melachouris, et al., European Patent Application Publication No. 0 087 247. In any event, when the present invention is employed as a final hydrolysis stage, the substrate, i.e., a hydrolysate, to be so hydrolyzed is treated so that mesophilic microorganisms and spores in the substrate are rendered non-viable, and then, the substrate is hydrolyzed with an enzyme preparation, as described above.

In particular, before hydrolysis in accordance with the present invention and/or before and/or between stages of a multi-step procedure, it may be found to be advantageous to heat the proteinaceous substrate to denature the protein, which thereby unfolds the protein/peptide structure and renders the substance more susceptible to enzymatic attack and cleavage. Likewise, conditions of pH may be altered between stages to accommodate a character of a different enzyme preparation employed in a subsequent stage and/or the nature of the substrate. As will be appreciated, operating with heat to render the substrate devoid of viable microorganisms and spores in the manners discussed further below will effect denaturation also.

The enzyme preparations employed in accordance with the present invention may be rendered substantially sterile by removing microorganisms and spores from the preparation or by subjecting the enzymes to procedures which render microorganisms and spores non-viable, but which do not affect the viability and activity of the enzyme preparation. A preferred means of obtaining sterile enzymes is by sterile filtration of a solution of the enzyme preparations, and in addition to membrane filters known in the art, useful systems for carrying such out are UNIFLO syringe filters, as may be obtained from Schleicher and Schuell, Inc., Keene, N.H., U.S.A. Also useful is a PROFLUX M12 tangential filtration system, which may be obtained from Amicon, Inc., Beverly, Mass., U.S.A.

As indicated above, it is considered that a sterile enzyme preparation is one which does not contain viable microorganisms or spores which will not pass through a filter having 0.45 μ pores. However, smaller pore filtration may be employed, and it may be preferred, as a safety-net, to exclude microorganisms and spores capable of passing through a membrane, i.e., filter, having 0.22 μ pores.

In addition, a sterile enzyme preparation may be obtained by irradiating an enzyme preparation, such as with ionizing radiation as disclosed in German Democratic Republic Patent Document DD 237 078 A3, or such may be obtained by acetone or alcohol precipitation methods known in the art. On the other hand, should a sterile enzyme preparation be available, such as in a form of a powder, and if the preparation is desired to be diluted in water, sterile water must be used.

In all events, after the sterile enzyme preparation has been obtained, it should be handled in accordance with good sterile/aseptic practice for use in accordance with the present invention.

With regard to rendering the substrate to be hydrolyzed in accordance with the present invention devoid of viable mesophilic microorganisms and spores, when a multistage hydrolysis is carried out, it has been found that reference may be had to whether or not prior processing has induced spores to an outgrowth stage, such being dependent upon, primarily, the conditions of temperature employed. For example, if a three-stage hydrolysis procedure is employed, one may simply heat the first hydrolysate, i.e., solubilized substrate, at a temperature and for a time sufficient solely to render viable microorganisms non-viable, i.e., killing the microorganisms only. In this case, although some spores may be rendered non-viable, the remaining spores will be induced to what is known as an outgrowth stage. Conditions then are maintained for a time at a temperature favorable for the spores to regenerate and transform into viable microorganisms and grow, i.e., on the order for up to about 2 hrs or so, and then, the substrate is heated at a temperature sufficient and for a time sufficient to render the microorganisms non-viable, this multi-step procedure thereby effectively rendering the substrate free of viable microorganisms and spores.

From a practical standpoint, in the context of a three-stage hydrolysis procedure, the outgrowth stage is allowed to proceed during a second hydrolysis step, and after that hydrolysis step, the hydrolysate is heated to render the microorganisms non-viable, which thereby will provide the necessary character of the substrate for proceeding with the process employing a sterile enzyme preparation. In general, therefore, in such a procedure, one may employ a temperature and a time sufficient to inactivate the enzyme(s) and/or a temperature employed in conventional pasteurization procedures. Thus, temperatures on the order of, generally, at least about 80° C. may be employed. However, as a safety-net, generally, a temperature on the order of at least about 90° C. is employed for a time sufficient to render the microorganisms non-viable, i.e., from about 5 mins to about 30 mins, and preferably, temperatures on the order of from about 90° C. to about 110° C. are employed most advantageously.

Heating for inactivation/pasteurization may be carried out batchwise, preferably with stirring, or with other agitation, using steam injection, or a jacketed tank or a suitable plate-type heat-exchanger, with or without steam injection, or continuously in a tube, preferably employing steam injection and static mixing elements.

On the other hand, to obtain a substrate devoid of viable microorganisms and spores, the substrate, e.g., hydrolysate, may be heated in suspension batch-wise or continuously with steam at temperatures of at least about 121° C. under a pressure of 15 psi (i.e., in excess of about 1 bar) for at least about 15 mins and in accord with art-accepted high or ultra-high-temperature/short-time sterilization procedures. This procedure must be carried out when the substrate to be treated in accordance with the present invention has not been subjected to conditions to induce an outgrowth stage, as discussed above. The sterilization may be carried out with the means mentioned above in connection with the inactivation/pasteurization procedure, but generally is carried out most advantageously with steam in a continuous mode in a tube containing static mixing elements.

Proteinaceous substances which may be treated usefully in accordance with the present invention include any edible protein substance, particularly food-acceptable substances.

In addition to the particular substances noted above, such proteinaceous substances include meat (including animal, fowl and fish meat) and bones, collagen, albumen and egg-yolk proteins and other phospho-proteins and protein-containing extracts thereof, and include derivatives of animal protein products, such as gelatin. Such substances also include dairy substances, including but not limited to whey proteins and casein, and include other protein-containing vegetable substances not mentioned above, such as protein-containing oil-seeds, in addition to soybeans, including defatted soybeans, and rice protein and quinoa. The proteinaceous substances also may include protein-laden substances and extracts obtained from microorganisms including cells of yeast and the like.

The enzyme preparation employed is dependent upon its composition and activity(ies) and is selected with a view to a desired end-product specification. The enzymes of the preparations may be natural, i.e., isolated from naturally-occurring microorganisms, or from genetically modified microorganisms ("GMO"), i.e., the products of genes which have been cloned and/or over-expressed, or may be enzymes which have been generated by mutagenesis. Enzymes which have been modified chemically, such as by immobilization or insolubilization including coating on beads or biological proteins or with such as PEG or pectin, also may be employed.

Although commercial-grade enzymes are employed most cost-effectively, particularly in cases in which a highest degree of control of final product specification profile is sought, an enzyme of highest purity may be employed, and since lesser amounts of enzyme may be employed in the process of the invention, as compared with the amounts employed conventionally to achieve a like result, e.g., a like degree of hydrolysis and product yield, purified and other enzymes not heretofore considered cost-effective may find applications which are cost/benefit effective.

Particularly in the case of commercial-grade enzymes, selection may be based with a view to the activities of "impurities", i.e., enzymes, as noted above, contained in an enzyme preparation other than the specific enzyme which has dominant activity. In this regard, as indicated above, it may be found that conditions of temperature may be manipulated to enhance the desired dominant enzyme activity of the preparation and/or mute or enhance the activity of such "impurities", which heretofore is not known to have been proposed in the art. Moreover, enzymes active in the psychophilic temperature range also may find particular applicability, particularly when operating under some preferred conditions of temperature of the present invention noted above.

In the case of treating proteins, any proteolytic enzyme preparation may be employed, and reference may be had to Webb, *ENZYME NOMENCLATURE*, NC-IUBMB, ACADEMIC PRESS, Inc., 1992, which provides a compilation of enzymes and their uses and substrate cleavage designations. Any of acid-, neutral-, or alkaline-active proteases may be selected dependent upon the character of the substrate and desired processing conditions.

In general, for example, the proteolytic enzymes may be obtained from animal and vegetable sources and particularly, from microbial sources such as from *Aspergillus awamori, Aspergillus niger, Aspergillus oryzae, Aspergillus sogae, Bacillus subtills*, Mucor sp. or *Rhizopus oryzae*. Such enzymes include enzymes such as disclosed in the documents heretofore identified herein and in Nakadai, et al., U.S. Pat. No. 3,914,346, for example, the disclosures thereof being incorporated herein by reference. However, although generally considered expensive to employ in an industrial context for producing food products, trypsin and chymotrypsin also are employed usefully, and pancreatin, which provides both lipolytic and proteolytic activity, may be employed usefully in certain cases.

Particularly, however, for reason of expense, when processing under acid conditions, an acid protease, such as may be obtained from QUEST International of Sarasota, Fla., U.S.A., and known as BIOCON Acid Protease or Acid Protease L preparations, may be employed usefully. When processing under neutral conditions, a neutral protease such as PROTEASE 2A, as may be obtained from Amano International Enzyme Co., Inc. of Troy, Va., U.S.A., may be employed usefully, and when processing under alkaline conditions, an ALKALASE 2.4 L preparation, as may be obtained from Novo Nordisk A/S of Bagsvaerd, Denmark, may be employed usefully.

To obtain products having high levels of free amino acids, any of various exopeptidase preparations may be employed. Aminopeptidase enzymes such as disclosed in the Nakadia '436 patent, the disclosure of which is incorporated herein by reference, may be employed usefully, although depending upon desired results, selection from any of those identified in *ENZYME NOMENCLATURE* may be made. A particularly useful aminopeptidase enzyme preparation includes a PEPTIDASE A AMANO preparation available from Amano which, as will be noted, also has endopeptidase activity. COROLASE enzyme preparations, which are supplied by Rohm Tech, Inc. of Malden Mass., U.S.A, and which may have exo- or endo-peptidase activity, are usefully employed, and it will be found that COROLASE PP has carboxypeptidase B activity. Also usefully employed are FLAVOURZYME enzyme preparations by Novo, which may include carboxypeptidase activity. It also may be found that PROMOD peptidase enzymes, available from BIO-CATALYSTS LTD, Pontypield, Wales, U.K., usefully are employed for hydrolyzing soy protein.

As also will be appreciated, carboxypeptidase preparations identified in *ENZYME NOMENCLATURE* may be used.

To obtain products having high levels of glutamic acid and/or glutamyl peptides, the "PGase" enzyme disclosed in the Kikuchi '967 patent noted above may be employed, and again, such enzymes as identified in *ENZYME NOMENCLATURE* may be used.

Although teachings in the art focus upon activity unit levels of enzymes and enzyme preparations, i.e., units/g such as Anson units/manufacturer's units, for example, for which cross-correlation generally is difficult without carrying out tests, such is not a variable of criticality or of any particular significance in the context of carrying out the concept of the present invention. However, of course, one should take into account a manufacturer's indications of activity and use levels and specifications.

In addition, it has been found that operating in accordance with procedures of the present invention reduces a total amount of enzyme employed to achieve a degree of hydrolysis equivalent with and generally greater than that which would be expected when operating in accordance with prior procedures. For example, in general, enzyme amounts employed may be on the order of up to 50% less that generally recommended by enzyme suppliers and/or generally used in any particular application. As also exemplified below, desirable results and high yields may be obtained by using enzyme amounts of the order of 1%, or less, by weight based upon the dry weight of the substrate.

The hydrolysis procedures of the present invention may be carried out batchwise, as long has been conventional in the art, or by procedures such as set forth in the Jost patent, noted above. A continuous ultrafiltration membrane reactor also may be employed, and circulation tube reactors may be employed usefully including, such as disclosed by Oosterhuis, et al., U.S. Pat. No. 5,073,496. Continuously operating in a manner as disclosed in Baensch, et al., European Patent Application Publication No. 0 566 877 is possible. Fixed enzyme reactors also may be considered. In this regard, as will be appreciated, differing equipment and processing configurations generally will affect such as reaction kinetics and reaction inhibition limits, because of such as differing ratios, over time, between reactants and reaction product because of differences in modes of operation.

Thus, as further will be appreciated from the disclosures of Jost, in particular, hydrolysis of milk proteins, and whey proteins in particular, may be carried out in at least two stages with heat denaturation steps and with enzymes such as trypsin, chymotrypsin and pancreatin and ALKALASE preparation. In accordance with the present invention, however, to achieve the final product specification, the final hydrolysis stage is carried out in a sterile system with sterile enzyme and with a hydrolysate devoid of viable mesophilic microorganisms and spores.

When carrying out a multi-stage process, processing conditions employed for effecting solubilization and/or proteolysis, prior to carrying out the enzymatic procedure in accordance with the invention, may include any of various conditions sufficient to optimize solubilization and/or hydrolysis reaction rate and product yield as are known in the art. However, in general, processing temperature conditions for proteolysis procedures employed prior to employing the process of the present invention desirably are in excess of the mesophilic range, which will assist in inducing outgrowth of spores, and such temperatures preferably are, as is conventional in the art, in excess of 50° C., for inhibition of microorganism growth.

As indicated above, the process according to the present invention is carried out advantageously at a temperature below the mesophilic range and preferably below about 17° C., which further reduces potential contamination by unwanted microorganisms. Although such temperatures may be below optimum ranges for a variety of enzymes and thus slow reaction rates, the reaction may be carried out for longer periods, which are on the order of days, rather than hours, and may be carried out beyond a point in time when the reaction rate begins to decrease. As indicated above, enzyme amounts on the order of 1%, or less, based upon the weight of the substrate, are employed advantageously.

Upon having carried out hydrolysis in accordance with the present invention for the time desired, assuming one is not employing a membrane reactor, one may heat the entirety of the hydrolysate, i.e., the supernatant and solids of the substrate hydrolyzed (the solids herein referred to as the "pelletized substrate"), to a temperature and for a time at least sufficient to inactivate the enzyme(s), or for a temperature and time sufficient to obtain a pasteurized or sterile/aseptic product. In the latter case, the product could be packaged aseptically, if desired. On the other hand, the supernatant may be separated from the pelletized substrate, which may be the case if employing a membrane reactor in a continuous mode, and so treated. In general, however, separation of supernatant from the pelletized substrate may be effected by filtering, but preferably by centrifugation which, in general, will provide higher supernatant yields, or a combination of filtering and centrifugation.

Alternatively, the enzyme-inactivated supernatant and pelletized substrate together, or the supernatant separated from the pelletized substrate may be used as is, or the supernatant may be concentrated, such as with vacuum evaporation, and/or dried by any of various drying procedures known in the art including, in particular, spray-drying or freeze-drying. Further alternatively, a supernatant may be subjected to ultrafiltration or other separation/fractionation techniques to obtain product fractions.

In addition, product yields may be increased further by treating the pelletized substrate from which supernatant has been separated with the same enzyme preparation or with a different enzyme preparation. In this regard, it has been found that the pelletized substrate retains not insignificant amounts of hydrolysate product, even after such as centrifugation. This product may be removed from the pelletized substrate such as by pressing or otherwise extracting the same. It also has been found that this hydrolysate has a character and composition different from that of the previously removed supernatant. In addition, the remaining pelletized substrate may be hydrolyzed further.

Furthermore, it should be noted that procedures in accordance with the present invention may be carried out with enzymes being added sequentially in one or more steps at differing points in time, which enables further product tailoring and/or yield increase. For example, an enzyme or enzymes may be employed to obtain a product predominant in di-, tri- and/or poly-peptides over a certain period of time and then, an enzyme preparation having particular activity may be added for cleaving the peptides, thus shifting the reaction equilibrium for enhancing at the same time, production of di-, tri- and/or poly-peptide products. Illustrative is employing first an enzyme preparation for obtaining glutamine and then subsequently, while that reaction is on-going, introducing an enzyme preparation suitable for cleaving the glutamine to obtain glutamic acid. Similarly, x-prolyl dipeptidase (pro-x) and x-pro dipeptidases usefully may be so employed to obtain proline.

In addition, pronase, extracellular proteins excreted by *Streptomyces griseus* may be employed in accordance with the present invention particularly usefully for obtaining high levels of free amino acids and may be used alone, or in combination with or in sequence with other enzymes. Also microbial collagenase, clostridio-peptidase A, will be found useful alone or together with other enzyme preparations suitable for hydrolyzing collagen.

As indicated above, the present invention is particularly usefully employed for hydrolyzing wheat gluten, soy protein and corn protein in a multi-step process which employs an exopeptidase, particularly an aminopeptidase, in a final step in accordance with the process of the present invention enables achieving a high degree of hydrolysis. It will be found, particularly with certain embodiments described further below, that a yield of free amino acids and peptides having a molecular weight of less than about 2,000 Daltons (i.e., chain length of up to 20 amino acids) contained in the hydrolysis supernatant and in the pelletized substrate on the order of at least about 65% and generally from about 65% to at least about 80%. Amounts of free amino acids in the supernatant may be found to be on the order of from about 40% to about 60%.

In the following discussion, reference to alkaline conditions is intended to mean and include a medium having a pH of about 7.5 and above and in particular, a pH of from about 8 to 12 and more particularly, from about 8.5 to 11. Neutral conditions are intended to mean and include a medium having a pH of from about 6.5 to about 7.5, and acid conditions are intended to mean and include a medium having a pH of less than about 6.5 and in particular, from about 2 to about 6.5 and more particularly, from about 3 to 4.

To achieve the afore-noted results readily with practice of the present invention, in the case of a corn protein substrate, corn protein is solubilized at least partially under alkaline conditions such that it is in a condition suitable for attack by proteolytic enzymes. A first hydrolysis step, which may be preceded by a heat denaturation step, is carried out under alkaline conditions with a protease which is active under alkaline conditions. ALKALASE 2.4 L enzyme preparation is employed usefully, and the reaction is carried out for a time such that the reaction is tended to be inhibited, i.e., to a point of reaction rate decrease, although longer times are not intended to be precluded.

After the first hydrolysis step, the proteolyzed corn substrate is heated at a temperature sufficient and for a time sufficient to render mesophilic microorganisms and spores non-viable. Since processing of the corn protein in this manner will provide desirable results in only a two-step hydrolysis procedure, the heating should be carried out so that the substrate is held at a temperature of at least about 121° C. for at least about 15 mins. under a pressure of at least about 15 psi (about 1 bar). The heated hydrolysate then is cooled and treated with a sterile enzyme preparation in a sterile system in accordance with the present invention described above to hydrolyze peptides, and preferably with an exopeptidase and preferably for a time which preferably ranges at least until a rate of hydrolysis begins to decrease. PEPTIDASE A AMANO preparation is usefully employed.

In the case of wheat protein, particularly gluten, a three stage hydrolysis process is carried out. The protein is placed in an acidic medium, i.e., acidified water, and then first treated with an acid protease to solubilize the intact protein at least partially and initiate hydrolysis, and this reaction may be carried out until the reaction rate begins to decrease, although longer times are not intended to be precluded. BIOCON acid protease preparation is employed usefully. The reaction medium is neutralized and heated to inactivate the enzyme preparation and render mesophilic microorganisms non-viable, such as by heating at about 100° C. to 110° C. for at least about 5 mins, but generally preferably, for at least about 10 mins.

After cooling, the substrate is treated with a neutral protease to hydrolyze peptides and any intact protein to obtain a second hydrolysate, and this reaction, too, may be carried out until the reaction rate begins to decrease, although longer times are not intended to be precluded. PROTEASE 2A preparation is employed usefully. This second hydrolysis also operates to effect a spore outgrowth stage and thus, the substrate medium need only be treated with heat to inactivate the enzyme preparation and render mesophilic microorganisms non-viable, such as in the manner noted above. However, use of a sterilization procedure is not intended to be precluded.

After cooling, the second hydrolysate is treated with a sterile enzyme preparation in a sterile system in accordance with the present invention described above to hydrolyze peptides, preferably with an exopeptidase and preferably for a time which preferably ranges at least until a rate of hydrolysis begins to decrease, although longer times are not intended to be precluded. Again, PEPTIDASE A AMANO preparation is employed usefully.

In the case of soy protein, a three stage hydrolysis procedure also is employed. The protein is suspended in water under alkaline conditions and is treated in an alkaline medium with an alkaline protease which further solubilizes the protein and effects hydrolysis, and this reaction may be carried out until the reaction rate begins to decrease, although longer times are not intended to be precluded. ALKALASE 2.4 L preparation is employed usefully, and prior to termination of this first hydrolysis stage, it may be found useful to reduce the pH to the neutral range, although such should not be deemed to be required.

The first soy hydrolysate reaction medium if not neutralized previously, may be neutralized and then it is heated to inactivate the enzyme preparation and render mesophilic microorganisms non-viable such as by heating at about 100° C. to 110° C. for at least about 5 mins, but generally preferably, at least about 10 mins.

After cooling, the first hydrolysate is treated under neutral conditions with a neutral protease to hydrolyze peptides and any intact proteins, and this reaction, too, may be carried out until the reaction rate begins to decrease, although longer times are not intended to be precluded. PROTEASE 2A preparation again is employed usefully. This second hydrolysis also operates to effect a spore outgrowth stage and thus, the substrate medium need only be treated with heat to inactivate the enzyme preparation and render mesophilic microorganisms non-viable, such as in the manner noted above. However, again, use of a sterilization procedure is not intended to be precluded.

After cooling, the second hydrolysate is treated with a sterile enzyme preparation in a sterile system in accordance with the present invention described above to hydrolyze peptides, preferably with an exopeptidase and preferably for a time which preferably ranges at least until a rate of hydrolysis begins to decrease. Again, PEPTIDASE A AMANO preparation is employed usefully.

As will be appreciated from the foregoing, any of known hydrolysate products may be produced by operating in accordance with the present invention, and such may be used in any of various known manners. Thus, such products and uses include nutritional products and uses, including hypoallergenic products such as foods for infants, or products which are specifically tailored for a particular use, including treatment of humans in need of one or more free amino acids, or small peptides, i.e., 2–5 amino acids, or for further processing to prepare further products. In particular, hydrolysates having high levels of free amino acids, and/or fractions thereof, may be employed usefully as flavorants per se or as precursors for other products including, in particular, precursors for flavorant production by such as a Maillard reaction or by other flavorant production reactions.

EXAMPLES

The following Examples are presented to illustrate further the present invention. Unless otherwise indicated, percentages are set forth by weight or by volume/volume.

Test Methods

Total amino acids in a product are determined by hydrolyzing a freeze-dried product with hydrochloric acid followed by HPLC procedures. A sample is introduced with 6M HCl into a Pierce hydrolysis tube and mixed. To facilitate placing the sample under vacuum, the sample contained in the tube is frozen, and vacuum is applied to effect a vacuum in the tube and the tubes are sealed. The sample under vacuum then is heated at about 110° for about 24 hrs to effect hydrolysis. After cooling, the hydrolysate obtained is vacuum-dried, and the dried sample is suspended in Pickering diluent buffer 2.2. The Pickering buffer sample is micro-centrifuged, and the supernatant is ultrafiltered through a 30,000 MW cut-off membrane. An aliquot is loaded on a Pickering amino acid analysis column which is used with a VARIAN 5500 HPLC system. The amino acids are eluted with a pH gradient and are detected after a post-column reaction with ninhydrin which is carried out in a Pickering apparatus.

The amount of free amino acids in a product is determined by suspending a sample in Pickering diluent buffer 2.2 and then centrifuging, filtering and analyzing as above.

Cell counts are performed by performing ten-fold serial dilutions of a sample in an aqueous sterile recovery diluent containing 8.5 g NaCl and 1 g peptone per 1. 0.1 ml aliquots of the diluent samples are spread-plated on DIFCO plate count agar (PCA) plates. The plates are incubated at 37° C. for about 2 days and the colonies are counted.

EXAMPLE I

Approximately 2 l of a 0.19% ortho-phosphoric acid solution prepared with deionized water is heated in a flask to about 75° C. 200 g of wheat gluten is added to the acid solution, and the mixture is mixed at high speed in a WARING blender to place the gluten in suspension. Prior to cessation of the mixing, 0.5 g of acid protease (BIOCON 200,000 BU/g) is added into the acidified suspension to obtain the preparation in the substrate in an amount of about 0.25% based upon the gluten substrate. The suspension is found to have a pH of about 3.5.

The acidified gluten/enzyme mix is placed in a flask which is covered and placed in a shaker incubator. The flask and contents are shaken sufficiently to maintain the gluten/enzyme mix suspended and are heated at about 60° C. for about 16 hrs, this incubation operating to solubilize the intact proteins partially and initiate a hydrolysis reaction and provide a reaction mix substrate (hydrolysate I). After incubation, a sample is taken from hydrolysate I for a cell count, which indicates that the microorganism cell number is less than 300 CFU/ml.

2.5M NaOH is added to and mixed with the hydrolysate I substrate in an amount sufficient to raise the pH of the mix to a pH of about 6.2. The flask is covered and placed in an autoclave and heated at about 104° C. for about 5 mins, which operates to inactivate the enzyme preparation, render mesophilic microorganisms non-viable, which thereby also denatures peptides. The flask and heated hydrolysate I are cooled to about 50° C.

One g of PROTEASE 2A preparation (>20,000 Amano units/g) is added to cooled hydrolysate I to provide the preparation in an amount of about 0.5% based upon the gluten initially employed. The flask is covered and placed in a shaker incubator, and the hydrolysate I/enzyme suspension is heated to a temperature of about 50° C. for about 7 hrs, with shaking sufficient to maintain the mix in suspension, to provide a second hydrolysate product (hydrolysate II) and which also results in a spore out-growth stage which yields microorganisms. A sample is taken for a cell count, which indicates that the cell number is less than $2 \times 10^3$ CFU/ml.

The flask containing hydrolysate II is covered and placed in an autoclave and heated at about 104° C. for about 10 mins, which operates to inactivate the protease, again denature peptides (and any remaining intact proteins) and to render mesophilic microorganisms non-viable. The covered flask and heated hydrolysate II then are cooled to room temperature (~22.5° C.).

2 g of PEPTIDASE A AMANO preparation (>100,000 aminopeptidase Amano units/g) is suspended in 15 ml sterile water contained in a sterile beaker. The suspension is filtered aseptically through a 0.45 µ membrane filter into cooled hydrolysate II to provide an enzyme preparation concentration of about 1% based upon the gluten initially employed, and the flask is covered.

The aminopeptidase/hydrolysate II reaction mix is cooled in the covered flask to a temperature of about 14° C., and to obtain a further hydrolysate product (hydrolysate III), the mix is maintained at about 14° C. for about 7 days, during which the flask is shaken at least daily to suspend separated solids. A sample is taken for a cell count, which indicates that the cell number is 0 CFU/ml, i.e., no detectable microorganism growth. Hydrolysate III then is heated at about 104° C. for about 5 mins to inactivate the enzyme.

Hydrolysate III is centrifuged at about 5,000 rpm for about 5 mins which provides a supernatant and a pelletized substrate.

The supernatant is freeze-dried, and 122 g of freeze-dried material is obtained.

Samples are taken from the freeze-dried material. Amino acid analysis indicates that the material contains about 64.3% total amino acids and that about 39.8% of the total amino acids is free amino acids.

COMPARATIVE EXAMPLE A 2 l of a 0.425% ortho-phosphoric acid solution is heated as in Example I, and 200 g of wheat gluten is added and mixed with the solution, also as in Example I. 4 g of acid protease (BIOCON 200,000 BU/g) is added to the acidified gluten suspension as in Example I to provide the preparation in an amount of about 2% with respect to the gluten substrate. The acidified gluten/enzyme mix is shaken and incubated as in Example I except that it is heated at about 65° C. and only for about 5.5 hrs. At the termination of this procedure, which provides a reaction mix substrate (hydrolysate IA), a sample is taken for a cell count, which indicates that the cell number is less than 300 CFU/ml.

The pH of hydrolysate IA is raised to about 6.3 with 2.5M NaOH, and then, hydrolysate IA is heated in an autoclave as in Example I for about 5 mins and then cooled to about 45° C.

4 g of PEPTIDASE A AMANO preparation (>100,000 Amano units/g) is added to cooled hydrolysate IA which provides the enzyme preparation in a concentration of about 2% based upon the gluten initially employed. The aminopeptidase/hydrolysate IA reaction mix are incubated at about 45° C. for about 6 hrs to obtain a further hydrolysate product (hydrolysate IIA). A sample is taken for a cell count, which indicates that the cell number is about 7,500 CFU/ml, which indicates that microorganisms are growing and which, in view of the time of the reaction, may indicate that microorganisms are approximately doubling each hour.

Hydrolysate IIA is centrifuged and the supernatant is freeze-dried as in Example I. Amino acid determinations indicate that the freeze-dried material contains about 68.1% total amino acids and about 26.6% of the total amino acids is free amino acids.

COMPARATIVE EXAMPLE B

An experiment is carried out in accordance with the procedures of COMPARATIVE EXAMPLE A, except that the amounts of enzyme preparation employed for each of the protease and aminopeptidase hydrolysis reactions are 1%, except that the acid proteolysis is carried out for about 14 hrs, except that the first hydrolysate product is heated in 10 mins, and except that the aminopeptidase hydrolysis is carried out at pH 7.3 for about 5½ hrs at 45° C. followed by 1 hr at 60° C.

The freeze-dried material contains about 62.7% total amino acids and about 24.2% of the total amino acids is free amino acids. The cell count after the acid proteolysis is less than 10 CFU/ml, and after the aminopeptidase hydrolysis, the cell amount is less than 15 CFU/ml.

EXAMPLE II 200 g of corn protein are added to about 2 l deionized water contained in a flask and having a temperature of about 75° C. 2.5M NaOH is added to the water and corn protein in amounts over time, while shaking the flask and contents with an incubator shaker to mix the ingredients and suspend the protein, to adjust the pH of the mix gradually to about 8.5. During mixing, the protein partially solubilizes, and prior to cessation of the mixing, 3 ml of ALKALASE 2.4 L preparation is added into and mixed with the corn protein substrate suspension to provide the preparation in a concentration of about 1.5% based upon the corn protein.

To obtain a first hydrolysate product (hydrolysate I), the flask is covered and the substrate/enzyme suspension is shaken sufficiently for about 7 hrs to maintain the corn protein/enzyme mix suspended while heated at about 55° C. 2.5M NaOH is added periodically during the first 6 hrs to maintain the pH at about 8, and then during the seventh hour, the pH is allowed to fall. A sample is taken for a cell count, which indicates that the microorganism cell number is below 1,000 CFU/ml.

The covered flask and hydrolysate I are heated in an autoclave at about 121° C. under a pressure of about 15 psi for about 15 mins and then, allowed to cool to room temperature (~22.5° C.).

2 g of PEPTIDASE A AMANO preparation (>100,000 aminopeptidase Amano units/g) is suspended in 15 mls water and aseptically filtered through a 0.45 µ membrane filter into cooled hydrolysate I to obtain an enzyme preparation concentration of about 1% based upon the corn protein initially employed, and the flask is covered.

To obtain a second hydrolysate product (hydrolysate II), the aminopeptidase/hydrolysate I reaction mix is cooled to and maintained at about 14° C. for about 6½ days with shaking as in Example I. Samples then are taken for cell counts which indicate 0 CFU/ml.

Hydrolysate II is centrifuged at 5,000 rpm for about 5 mins to obtain a supernatant and a pelletized substrate. The supernatant is freeze-dried, and 161 g of product is obtained.

The freeze-dried material contains about 43.9% total amino acids and about 48% of the total amino acids is free amino acids.

EXAMPLE III

Experiments are carried out in accordance with the procedures of Example I, but differ in the temperatures of the incubation of hydrolysate II with aminopeptidase, as indicated in the following Table. Samples to determine free amino acid content of the supernatant as a percentage of total amino acids are taken at various times, as also indicated in the Table, and the dashes indicate that samples are not analyzed.

| Time (hrs) | Temperatures | | |
|---|---|---|---|
| | 40° C. | 29° C. | 17° C. |
| | | Free Amino Acids % | |
| 0 | 17.25 | 17.25 | 17.25 |
| 5 | 26.7 | 25.6 | — |
| 9 | 28.8 | 25.9 | — |
| 12 | 32.3 | 31.6 | — |
| 27.5 | 34.7 | 37 | 23.3 |
| 54 | 41.9 | 45 | 30 |
| 96 | — | — | 35.4 |
| 168 | — | — | 42.9 |

EXAMPLE IV 200 g soy bean meal is added to 2000 ml water in a flask and agitated on a platform shaker at a temperature of about 60° C. for about 30 mins to suspend the meal. 2.5M NaOH is added to the suspension in an amount sufficient to adjust its pH to about 8. 3.5 ml ALKALASE 2.4 L preparation is added to the pH-adjusted suspension and heated at 60° C. for about 8 hrs to obtain a first hydrolysate (hydrolysate I).

Phosphoric acid is added to hydrolysate I in an amount sufficient to adjust its pH to about 6.5 and then, this pH-adjusted hydrolysate I is heated in an autoclave at a temperature of about 104° C. for about 5 mins and then cooled.

One g of PROTEASE 2A preparation (>20,000 Amano units/g; 0.5% enzyme) is added to cooled hydrolysate I and incubated in a shaker incubation at 50° C. for about 5 hrs to obtain a second hydrolysate product (hydrolysate II). Hydrolysate II is heated in an autoclave at 121° C. for 15 mins at a pressure of about 15 psi and then is cooled.

2 g of PEPTIDASE A AMANO preparation (>100,000 Amano units/g) are rendered sterile as in the Examples above, and the sterile enzyme preparation is added to cooled hydrolysate II which provides a preparation concentration of about 1% with regard to the soy meal initially employed. The temperature of hydrolysate II and the preparation are reduced to about 16° C. and incubated with an incubator shaker for about 4 days to obtain a further hydrolysate product (hydrolysate III).

Hydrolysate III is heated to inactivate the enzyme preparation, cooled, and centrifuged as in the Examples above. The supernatant is freeze-dried, and about 83 g of freeze-dried material is obtained which contains about 45% free amino acids as a percent of total amino acids.

As is clear from the foregoing, various modifications of the present invention may be made without departure from the spirit and scope of the disclosure, and the invention may be embodied and/or practiced suitably in the absence and/or to the exclusion of process steps and/or manipulations, conditions, substances and/or ingredients manipulated and/or limitations not specifically disclosed herein.

We claim:

1. A process for preparing a comestible hydrolysate product comprising hydrolyzing a proteinaceous substance with a proteolytic enzyme preparation to obtain a hydrolysate substrate, heating the hydrolysate substrate at a temperature sufficient for a time sufficient to obtain a substrate devoid of viable mesophilic microorganisms and spores and hydrolyzing the substrate devoid of viable mesophilic microorganisms and spores in a sterile system with a sterile enzyme preparation suitable for hydrolyzing the substrate.

2. A process according to claim 1 wherein the substrate is hydrolyzed at a temperature of from about 0° C. to about 45° C.

3. A process according to claim 1 wherein the substrate is hydrolyzed at a temperature of from about 0° C. to about 20° C.

4. A process according to claim 1 wherein the substrate is hydrolyzed at a temperature of from about 20° C. to about 40° C.

5. A process according to claim 1 wherein the enzyme preparation suitable for hydrolyzing the substrate comprises an exopeptidase preparation.

6. A process according to claim 1 wherein the enzyme preparation suitable for hydrolyzing the substrate comprises pronase.

7. A process according to claim 1 wherein the proteolytic enzyme preparation for hydrolyzing the proteinaceous substance comprises pronase.

8. A process according to claim 1 wherein the proteinaceous substance is a proteinaceous vegetable substance.

9. A process according to claim 1 wherein the proteinaceous substance is corn and the corn is hydrolyzed under alkaline conditions.

10. A process for preparing a comestible hydrolysate product comprising treating a food-acceptable proteinaceous substance with a proteolytic enzyme preparation to solubilize protein of the substance to obtain an at least partially solubilized substance, heating the at least partially solubilized substance at a temperature sufficient for a time sufficient to obtain a heat-treated substance devoid of viable mesophilic microorganisms, hydrolyzing the heat-treated substance with a proteolytic enzyme preparation to hydrolyze the heat-treated substance to obtain a hydrolysate substrate, heating the hydrolysate substrate at a temperature sufficient for a time sufficient to obtain a substrate devoid of viable mesophilic microorganisms and spores and hydrolyzing the substrate devoid of viable mesophilic microorganisms and spores in a sterile system with a sterile enzyme preparation suitable for hydrolyzing the substrate.

11. A process according to claim 10 wherein, to obtain the substrate devoid of viable mesophilic microorganisms and spores, the heat-treated substance is hydrolyzed at a temperature for a time favorable for spores to regenerate and transform into viable microorganisms and grow and the proteinaceous substrate is heated at a temperature sufficient for a time sufficient to render the substrate devoid of mesophilic microorganisms.

12. A process according to claim 10 wherein the substrate is hydrolyzed at a temperature of from about 0° C. to about 45° C.

13. A process according to claim 10 wherein the substrate is hydrolyzed at a temperature of from about 0° C. to about 20° C.

14. A process according to claim 10 wherein the substrate is hydrolyzed at a temperature of from about 20° C. to about 40° C.

15. A process according to claim 10 wherein the enzyme preparation suitable for hydrolyzing the substrate comprises an exopeptidase preparation.

16. A process according to claim 10 wherein the enzyme preparation suitable for hydrolyzing the substrate comprises pronase.

17. A process according to claim 10 wherein the proteolytic enzyme preparation for hydrolyzing the heat-treated substance comprises pronase.

18. A process according to claim 14 wherein the proteinaceous substance is a proteinaceous vegetable substance.

19. A process according to claim 14 wherein the proteinaceous substance comprises wheat gluten and the wheat gluten is treated in an acidic medium with an acid protease to obtain the at least partially solubilized substance and the heat-treated substance is hydrolyzed with a neutral protease.

20. A process according to claim 14 wherein the proteinaceous substance comprises soy protein and the soy protein is treated in an alkaline medium with an alkaline protease to obtain the at least partially solubilized substance and the heat-treated substance is hydrolyzed with a neutral protease.

* * * * *

UNITED STATES PATENT AND TRADEMARK OFFICE
CERTIFICATE OF CORRECTION

PATENT NO. : 5,618,689
DATED : April 8, 1997
INVENTOR(S) : James G. McCarthy, et al.

It is certified that error appears in the above-indentified patent and that said Letters Patent is hereby corrected as shown below:

Column 8, line 67, "3,914,346" should be --3,914,436--.

Column 9, line 20, "Nakadia" should be --Nakadai--.

Signed and Sealed this

Nineteenth Day of August, 1997

*Attest:*

BRUCE LEHMAN

*Attesting Officer*     *Commissioner of Patents and Trademarks*